United States Patent [19]

Gudin et al.

[11] Patent Number: 5,179,012
[45] Date of Patent: Jan. 12, 1993

[54] PROCESS FOR THE PRODUCTION AND EXTRACTION OF ANTIOXIDANTS FROM A MICRO-ORGANISM CULTURE

[75] Inventors: Claude Gudin, Aix en Provence; Catherine Thepenier, Manosque, both of France

[73] Assignee: Commissariat A L'Energie Atomique, Paris, France

[21] Appl. No.: 638,394

[22] Filed: Jan. 7, 1991

[30] Foreign Application Priority Data

Jan. 11, 1990 [FR] France .................... 90 00279

[51] Int. Cl.$^5$ .............. C12P 17/06; C12P 17/04; C12P 9/02; C12R 1/89
[52] U.S. Cl. ..................... 435/125; 435/41; 435/126; 435/136; 435/137; 435/170; 435/173; 435/189; 435/287; 435/296; 435/822; 435/946
[58] Field of Search .............. 435/41, 125, 126, 170, 435/173, 189, 822, 946, 136, 137

[56] References Cited

U.S. PATENT DOCUMENTS

| | | | |
|---|---|---|---|
| 3,997,402 | 12/1976 | Michelson | 435/189 |
| 4,022,604 | 5/1977 | Kawamura et al. | 435/125 |
| 4,029,819 | 6/1977 | Michelson | 435/189 |
| 4,217,728 | 8/1980 | Shimamatsu et al. | 47/1.4 |
| 4,320,050 | 3/1982 | Rebeller et al. | 435/946 |
| 4,563,349 | 1/1986 | Miyata et al. | 435/189 |
| 4,693,842 | 9/1987 | Shilo et al. | 435/84 |
| 4,774,185 | 9/1988 | Asami et al. | 435/822 |
| 4,906,746 | 3/1990 | Barnier et al. | 435/72 |
| 4,978,617 | 12/1990 | Furuya | 435/125 |

FOREIGN PATENT DOCUMENTS

A310522 4/1989 European Pat. Off. .

OTHER PUBLICATIONS

Chemical Abstracts, vol. 87, 1977 (Mistral et al.) No. 147729z.
Chemical Abstracts, vol. 74, 1971 (Antia et al.) No. 29131g.

*Primary Examiner*—Herbert J. Lilling
*Attorney, Agent, or Firm*—Pearne, Gordon, McCoy & Granger

[57] ABSTRACT

The process consists of culturing in a closed photobioreactor (2) microalgae suspended in a culture medium (1), the oxygen produced by the microalgae by photosynthesis being collected and then reinjected into the culture medium, separating (6) the microalgae from the culture medium (1), dissolving (12) the microalgae, grinding or crushing (14) the solution of microalgae, adding (16) a solvent to the ground or crushed solution for solubilizing the antioxidants produced by the microalgae and then separating (18) the liquid phases present.

17 Claims, 4 Drawing Sheets

PROCESS FOR THE PRODUCTION AND EXTRACTION OF ANTIOXIDANTS FROM A MICRO-ORGANISM CULTURE

The present invention relates to a process for the production and extraction of antioxidants from a culture of photosynthetic microorganisms suspended in a liquid medium, as well as the photobioreactor for culturing these microorganisms. This process permits an intensive, controlled production of antioxidants on an industrial scale.

The invention is applicable to the production of any antioxidant and in particular to the production of superoxide-dismutase enzymes, known by the abbreviation SOD of vitamin C, alpha, beta or gamma tocopherol, alpha tocopherol being vitamin E.

Superoxide-dismutases are metal enzymes having two peptide subunits linked to one another. There are three types of SOD classified as a function of the nature of the metal:

Cu/Zn SOD, which are frequent in eukaryocytes—the traditional source of said SOD being cattle blood and extraction takes place from erythrocytes;

Mn SOD found in eukaryocytes relative to mitochondria and in the prokaryocytes;

finally, the Fe SOD which would appear to be specific to prokaryocytes i.e. aerobic bacteria.

SOD's are dismutation catalysts of superoxide ions in accordance with the reaction:

$$O_2^- + O_2^- + 2H^+ \rightarrow H_2O_2 + O_2$$

Thus, SOD's are used in acute phenomena freeing superoxide radicals or in aging phenomena. They are in particular used in the pharmaceutical fields as anti-inflammatory agents, (rheumatism, arthritis), cosmetological agents for protecting the skin and hair, e.g. for protecting against ultraviolet rays, in the agro-alimentary field (for protecting oils and fatty substances, as a regulating agent of the coloring or as fertilizers, as well as in the biomedical field. Their use in cosmetology is in particular described in FR-A-2 297 899.

The invention is applicable to any photosynthetic microorganism of the microalgae type and the cyanobacteria type. One of the best known cyanobacteria is the "blue alga".

Photosynthesis is the tranformation by solar energy of carbon dioxide into primary hydrocarbon material, the oxygen being the main biproduct of this biochemical transformation. This reaction can be symbolized by the following Myers equation:

$$6.14\, CO_2 + 3.65\, H_2O + NH_3 \rightarrow C_{6.14}H_{10.3}O_{2.24}N + 6.85\, O_2$$

The term $C_{6.14}H_{10.3}O_{2.24}N$ corresponds to the microorganisms, also known as biomass.

In FR-A-2 621 323 filed on Oct. 2, 1987 in the name of the Applicant is described an apparatus for the intense, controlled production of photosynthetic microorganisms. Said apparatus is in particular a closed or sealed photobioreactor designed so as to control the monoculture of a desired species, as well as the parameters of the culture, such as the temperature, the pH, the $CO_2$ and $O_2$ pressures in the culture medium, as well as the composition of the nutrient medium, in order to favor the production of the selected species.

These photobioreactors essentially comprise a solar sensor or receiver which is transparent to light in which flows the liquid medium containing the microorganisms, a carbonator connected to the inlet of the solar sensor for supplying the liquid medium with the $CO_2$ necessary for the photosynthesis, as well as a degasifier connected to the photobioreactor for eliminating from the liquid medium the oxygen produced by the microorganisms, as well as the $CO_2$ not dissolved in the liquid medium.

The carbonator makes it possible to ensure an adequate transfer of $CO_2$ from the gas phase to the liquid phase, so that the biological demand for $CO_2$ is always satisfied. $CO_2$ is not then a limiting factor in the production of the microorganisms.

If the other culture conditions are favorable, such as light, the nutrient medium, the pH, etc., there is a high demand for $CO_2$, so that a large amount of oxygen is formed. In addition, in the solar receiver of the photobioreactor, there is an enrichment of the culture with dissolved $O_2$, as well as gaseous $O_2$ pockets.

FR-A-2 621 323 teaches elimination by means of a degasifier of the oxygen produced by photosynthesis prejudicial to the operation of the photobioreactor and in particular the good heat regulation thereof (drying of the microorganism and poor photobioreactor efficiency). In addition, oxygen can be toxic for certain microorganisms.

Contrary to the teaching of the aforementioned document, the inventors have found that the collection of the oxygen produced by photosynthesis and its reinjection in the culture medium makes it possible to obtain a significant antioxidant production by the cultured microorganism. Thus, under high oxygen content conditions, the photosynthetic microorganisms react to the oxydizing conditions by synthesizing antioxidants.

The invention therefore relates to a process for the production and extraction of antioxidants, comprising the following stages:

(a) culturing in a closed photobioreactor of photosynthetic microorganisms suspended in a liquid culture medium, the oxygen produced by the microorganisms by photosynthesis being collected and reinjected into the culture medium, said microorganisms being chosen from the group constituted by microalgae and cyanobacteria, (b) separation of the microorganisms from the culture medium, (c) dissolving the microorganisms separated in (b), (d) "crushing" the dissolved microorganisms, (e) addition of solvent to the solution obtained in (d) in order to solubilize the antioxidants produced by the microorganisms and then (f) separation of the liquid and solid phases present.

Advantageously, the oxygen is reinjected under pressure into the liquid medium.

the antioxidants produced are of different types and are a function of the cultured species.

The microorganisms to which the invention apply are all microalgae and cyanobacteria which are known. The microalgae are in particular rhodophyceae such as Porphyridium cruentum which, under oxidizing conditions, essentially permits Mn SOD production. This SOD is constituted by two subunits each of 20,000 molecular weights, which are linked by non-covalent bonds. It has a mean isoelectric point of 4.2.

On average, Porphyridium cruentum produces 10 to 20 U, according to analysis of NBT (nitroblue tetrazolium), per milliliter of culture (1 ml of culture containing approximately 1 mg of dry matter of microalgae). Porphyridium cruentum also makes it possible to produce vitamin C. Thus, this microalga contains 5 to 7 g/kg of vitamin C.

In this microalga, the "delta-amino-levulinic" metabolic route is very highly developed and leads to specific pigments (phycobiliproteins) and two SOD.

However, the culture of microalgae of the chlorophyceae type such as *Haematococcus pluvialis* essentially permits in the sugar oxidizing medium the production of tocopherals and in particular alpha-tocopherals (vitamin E) at a concentration of 4 to 5 g/kg of microalgae and gamma-tocopherals at a concentration of 0.5 to 1 k/kg of microalgae. In this microalga, the "mevalonic" metabolic route is very highly developed.

The conditions favorable for the production of antioxidants according to the invention are high oxygen production conditions, i.e. high photosynthetic activity. In addition, advantageously, the culture of microorganisms is carried out under conditions of natural lighting and the extraction of the antioxidants from the culture medium, and consequently the stage (b) of separating the microorganisms from the liquid medium are carried out in the afternoon.

In addition, the most favorable conditions for the production of antioxidants are those where the microorganisms are in the exponential growth phase, i.e. when the growth rate is at a maximum.

For continuous or batch operation, the exponential phase is at the start of culturing. The microorganisms are in the active division phase, which corresponds to a maximum photosynthetic activity. In the case of continuous culturing, it is necessary to choose a rapid replacement rate for the culture medium (0.2 to 1 every day) in order to maintain the microorganisms in the active division phase.

Before separating the microorganisms from the culture medium, it is possible to carry out one or more treatments of the suspension of the microorganisms with a view to increasing the culture medium content of antioxidants and in particular SOD by increasing the membrane permeability of the cells.

This or these treatments can consist of heating an cellular suspension for a few minutes at between 40° and 50° C. or an ionization of said suspension with gamma rays. A treatment of 10 kgrays can lead to a 20 to 100% antioxidant activity enrichment of the medium.

Stage (b) of separating the microorganisms from the culture medium serves to separate the biomass, the intracellular antioxidants being extracted during stages (c) and (f) from the culture medium, which can contain exocellular antioxidants.

In the particular case of SOD's, more than half the enzymes are in the culture medium and the activity measured therein can, in certain cases, justify the treatment of the liquid medium in order to extract therefrom the exocellular antioxidants.

The dissolving of the microorganisms (stage c) makes it possible to adjust the concentration of the juice of the microorganisms with a view to improving the crushing conditions. The optimum microorganism concentration for the crushing stage is between 20 and 100 g/liter of dry matter, as a function of the species used and their growth stage.

The "crushing" stage serves to shatter or burst the microorganisms in order to render the entire cellular content accessible to the solvent. It is carried out in a homogenizer, where the microorganisms are subject to an alternation of pressures and vacuums.

The solvent or solvent mixtures used in stage (e) is dependent on the antioxidants which it is wished to extract. In particular, the SOD's and vitamin C are hydrosoluble and their extraction takes place in aqueous solution, whereas the tocopherals are liposoluble and their extraction takes place in an organic solvent of the acetone or methanol type or in a vegetable or mineral oil.

If it is wished to extract both liposoluble and hydrosoluble antioxidants produced by the same species, an organic solvent or an oil is used.

The phase separation stage (f) serves to separate the mixture into two or three phases as a function of whether or not an aqueous solvent is used: an aqueous solution containing hydrosoluble antioxidants a lipid solution containing liposoluble antioxidants and a solid phase constituted by cellular residues. This phase separation can be carried out by centrifuging or by decanting in a pulsed column.

Preferably, the crushing, addition of solvent and separation of phases stages are carried out at approximately 4° C. If necessary, the lipid and aqueous phases obtained during stage (f), as well as the liquid medium resulting from the separation stage (b) for the microorganisms can be concentrated and optionally purified. Said concentrations can be carried out by ultrafiltration and/or by precipitation with ammonium sulphate. Purification is advantageously carried out at 4° C. and its degree is dependent on the use of antioxidants.

The invention also relates to a closed photobioreactor for the production of antioxidants from a culture of photosynthetic microorganism suspended in a liquid medium, said microorganisms being chosen from the group constituted by microalgae and cyanobacteria, said photobioreactor comprising:

(A)—A solar receiver transparent to sunlight in which circulates the liquid medium, (B)—a column carbonator connected to the intake of the solar receiver for supplying the liquid medium with the $CO_2$ necessary for photosynthesis, (C)—a collector of the oxygen produced by the microorganisms by photosynthesis and (D)—means for reinjecting the collected oxygen with respect to the carbonator.

To obtain a maximum photosynthetic activity, the solar receiver comprises parallel tubes in which circulates the liquid medium, end collectors ensuring the linking of the said tubes.

BRIEF DESCRIPTION OF DRAWINGS

The invention is described in greater detail hereinafter relative to non-limitative embodiments and the attached drawings, wherein show:

As shown in FIG. 1, the *Porphyridium cruentum* culture 1 takes place in a photobioreactor 2 containing as the nutrient medium synthetic sea water enriched with potassium, phosphorus and nitrogen. The potassium is present in chloride form, the phosphorus in orthophosphoric acid form and the nitrogen in the form of urea and nitrates.

Figure 1:
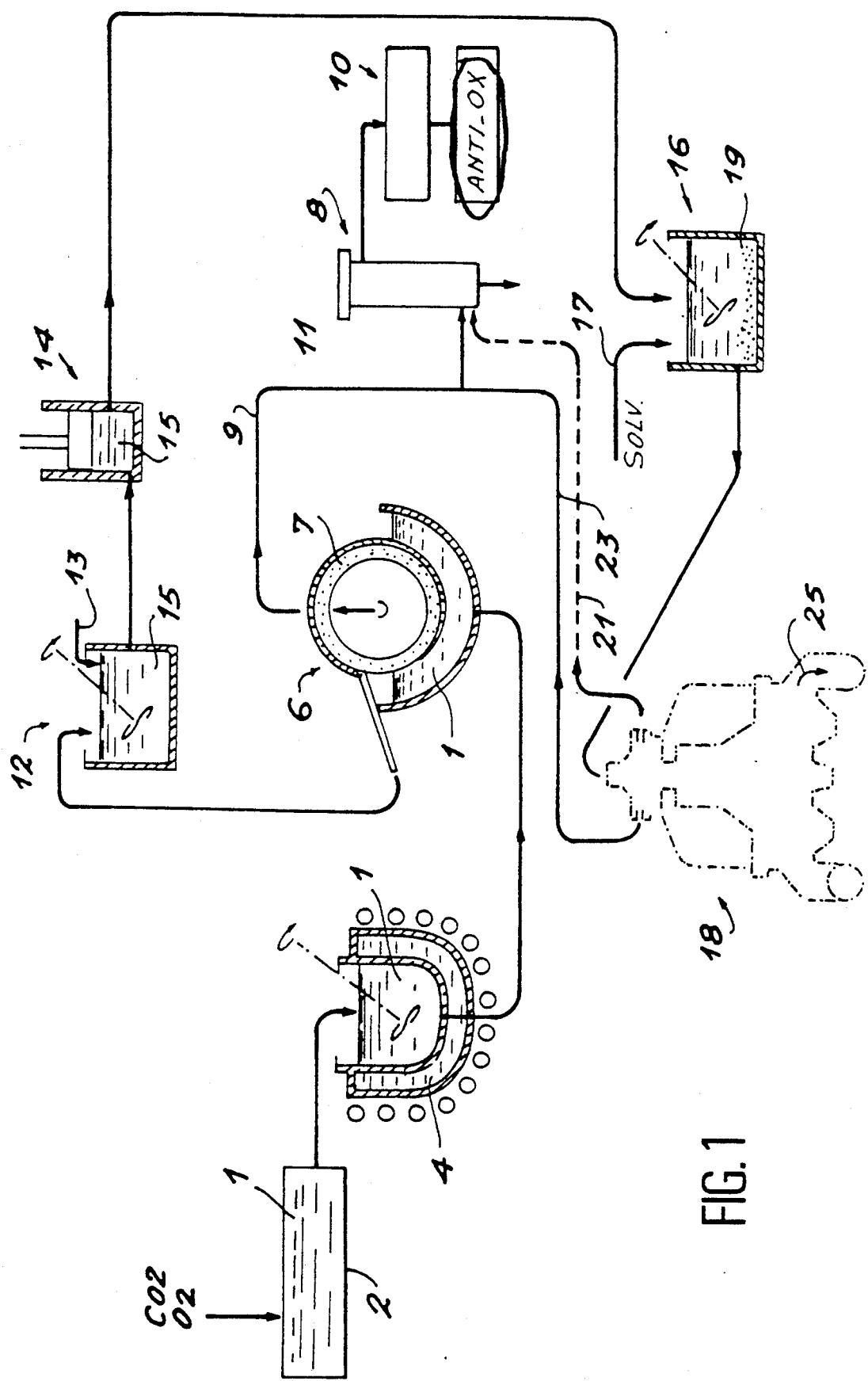
FIG. 1 diagrammatically the different stages of the extraction process according to the invention of antioxidants from a culture of microalgae.

The pH of the culture medium is regulated between 6 and 8 throughout the growth of the microalgae and the carbon supply takes place in the form of carbon dioxide. The precise construction of this photobioreactor will be described relative to FIGS. 2 and 3.

The culture of microalgae takes place over several days and the culture medium contains approximately 1 g/liter of dry matter of microalgae. The production of these microalgae takes place under natural lighting conditions and the treatment of the microalgae for extracting therefrom the antioxidants lasts between 12 and 18 hours and in an exponential growth phase for the same.

The culture removed from the photobioreactor is placed in a water bath 4 heated to between 40° and 50° C. for 10 to 20 minutes, with a view to increasing the membrane permeability of the microalgae and consequently the content of exocellular antioxidants. This heating is accompanied by stirring.

As indicated at 6, the culture 1 is then filtered on a rotary filter 7 with a flow rate of close to 200 l/h/m$^2$, in order to separate the microalgae from the liquid medium. This stage can also be performed on a continuous centrifuge between 10,000 and 30,000 g with a flow rate of 1 m$^3$/h. The clear filtrate 9 obtained in 6 contains more than half superoxide-dismutase enzymes. In particular, the enzymatic activity measured in the liquid medium is 10 to 30 U/m, the measurement being carried out by NBT.

The SOD's are directly in aqueous solution can then be concentrated in the manner indicated at 8 by ultrafiltration with a 10,000 daltons mineral membrane. The thus concentrated filtrate 9 can be purified, as indicated at 10 and in particular by anion exchange chromatography. The stages of concentration 8 and purification 10 are performed at approximately 4° C.

The solid product obtained 6 essentially contains microalgae, which are diluted, accompanied by stirring and as indicated at 12, in a phosphate buffer solution (50 mM, pH 7.8) introduced at 13, in order to obtain an optimum microalgae concentration for the "crushing" stage 14. The microalgae concentration in the suspension 15 obtained at 12 is 20 to 100 g/l of dry matter (dm).

The suspension 15 is then subject to a pressure-vacuum cycle in an ATV homogenizer of the Manton-Gaulin type operating at a pressure of 2 to 5.10$^7$ Pa. This stage is preferably carried out at 4° C. It is used for shattering the microalgae, so that the entire cellular content is accessible to the solvents.

To the cellular suspension of *Porphyridium cruentum* obtained in 14 is added a vegetable or mineral oil, e.g. a soy oil or a solvent of the acetone or methanol type in order to extract both the liposoluble antioxidants such as the tocopherols and the hydrosoluble antioxidants such as vitamin C and SOD.

This solvent addition is represented at 16 and the arrow 17 indicates the solvent supply to the cellular suspension. This solvent addition takes place accompanied by stirring and at approximately 4° C. The cellular suspension obtained carries the reference 19.

As indicated at 18, the cellular suspension 19 is then centrifuged in a single-stage centrifugal extractor equipped with type VA 35-09-566 piston valves. The centrifugate obtained is particularly constituted by an aqueous solution containing SOD and vitamin C and a lipid solution containing tocopherols. Reference 21 corresponds to the recovery of the aqueous solution and reference 23 to the recovery of the lipid solution. These solutions can then be concentrated as indicated at 8, in the same way as the liquid medium obtained after separating the microalgae in 6. The solid residues obtained at 25 and resulting from centrifuging 18 contain fragments of microalgae.

Figure 2:
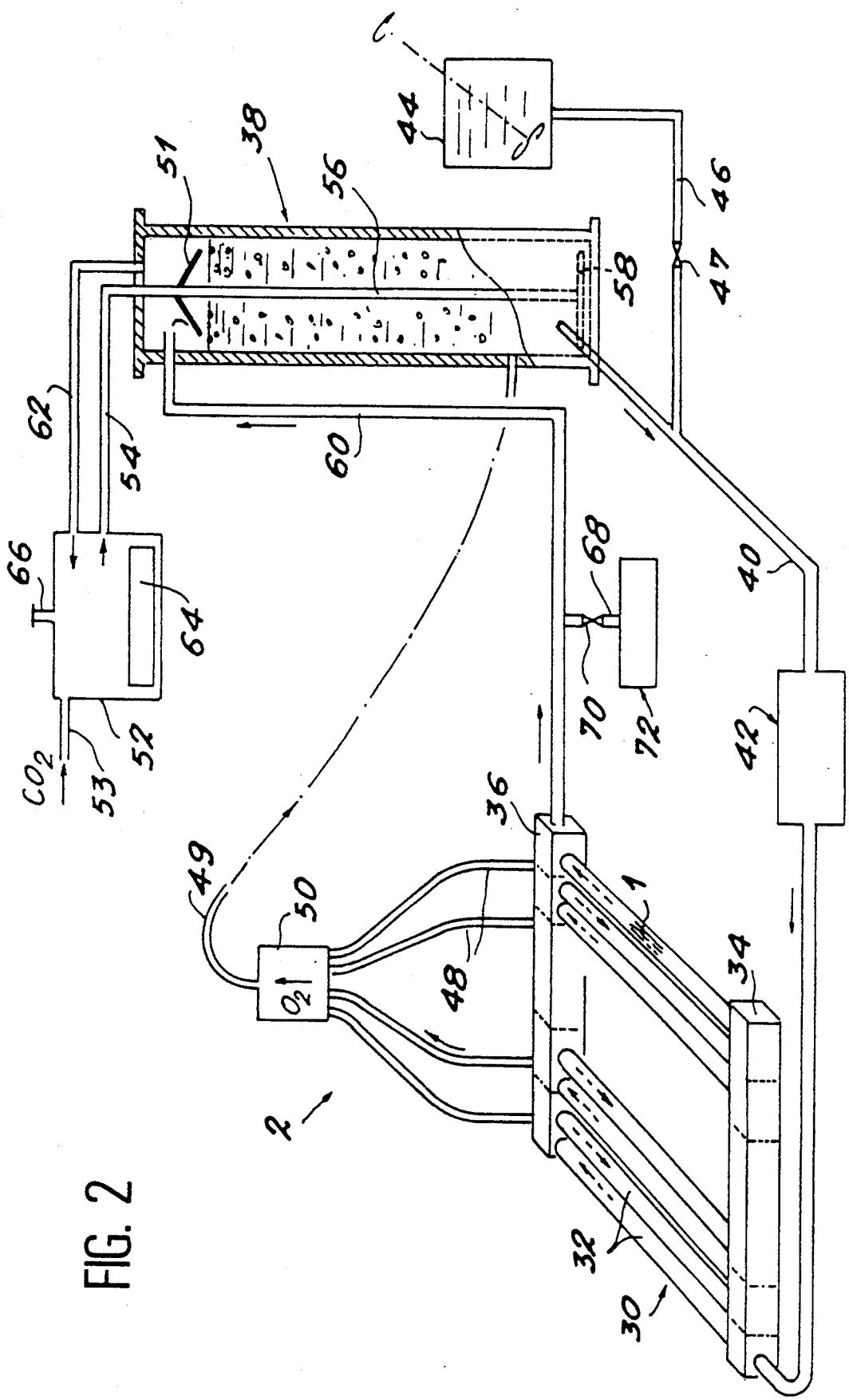
FIG. 2 diagrammatically a photobioreactor for the production of microalgae according to the invention and operating in batch manner.

FIG. 2 shows a photobioreactor according to the invention used for the batch culturing of microalgae or cyanobacteria, which produce antioxidants. The closed photobioreactor 2 has a solar receiver 30, constituted by parallel, flexible, transparent plastics material tubes 32, such as of polyethylene, in which circulates the culture medium 1 containing the microorganisms and the nutrient elements necessary for the growth thereof. The polypropylene collectors 34 and 36 make it possible to interconnects the tubes 32 and ensure the passage of liquid from one tube to the other. This solar receiver 30 is intended to be placed on the surface of an expanse of water for its heat regulation.

For further details concerning the construction and operation of the solar receiver or sensor reference can be made to the aforementioned FR-A-2 621 323.

The CO$_2$ supply for the culture medium during a cycle or run is provided by a carbonator 38 connected to the intake of the solar sensor 30, via a supply pipe 40. The latter is equipped with a pump 42 ensuring the circulation of the culture medium throughout the photobioreactor. The carbonator 38 is of the column type and the CO$_2$ supply for the culture medium via the pipe 40 takes place through the bottom of the carbonator.

The photobioreactor also has a vessel 44 used for the preparation, accompanied by stirring, of the nutrient medium necessary for the growth of the microalgae. This nutrient medium is introduced at the start of the run into the liquid medium containing the microalgae, using a supply pipe 46 branched to the supply tube 40. The branch pipe 46 is equipped with a valve 47 making it possible to control or check the injection of the nutrient medium.

In the solar receiver 30, the photosynthesis reaction leads to the formation of oxygen. Purge tubes 48 fitted at the outlet of the solar receiver 30 and more specifically at the outlet of the collectors 34 and 36 on make it possible to eliminate the gas pockets which form in the solar receiver tubes 32. This gas can contain up to 75% by volume of oxygen under high sunlight conditions for the solar receiver 30, said oxygen resulting from the photosynthesis.

This gaseous oxygen is collected in a collector 50 and then reinjected into the carbonator 38 with the aid of a pipe 49. The recycling of the gaseous oxygen takes place at the bottom of the carbonator 38.

In said carbonator, the oxygen is redissolved in the culture medium. In order to assist the passage of the oxygen into the culture medium, the upper part of the carbonator is equipped with a conical deflecting plate 51.

The supply of CO$_2$ into the carbonator 38 is carried out by mixing with air up to 80% by volume of CO$_2$. This gaseous mixture is introduced into a vessel 52 via a supply pipe 53.

The outlet of the said vessel is equipped with a supply pipe 54 connected to a central immersion tube 56 of the carbonator 38 and positioned along the axis of revolution of the latter. The immersion end 58 of the tube 56 is made from fritted or sintered stainless material or glass having a variable porosity in order to improve the countercurrent dissolving of the $CO_2$ in the liquid medium containing the microalgae. The introduction of the culture medium 1 into the carbonator takes place in the upper part of the latter by means of a supply pipe 60 connected to the outlet of the downstream collector 36 of the solar receiver.

The air-$CO_2$ mixture introduced into the carbonator 38 through the fritted glass 58 causes a slight desorption of the oxygen dissolved in the culture medium. The gaseous mixture discharged at the top of the carbonator is recovered by a discharge pipe 62 for reinjection into the vessel 52.

The gas from the said vessel 52 is compressed by a piston-type device 64 and reinjected into the carbonation column 39 via the pipe 54 and then the immersion tube 56. The said gas reinjected at the bottom of the carbonator contains desorbed oxygen and $CO_2$ not dissolved in the liquid phase. The vessel 52 is equipped with a pressostat 66, whose pressure level is regulated between 0.1 and $0.5 \cdot 10^5$ Pa. This system leads to a dissolved oxygen enrichment of the culture.

Under high sunlight conditions, the oxygen percentage in the gaseous phase is 21% by volume and at the intake of the supply pipe 53.

At the outlet from the carbonator 58 or at the inlet of the solar receiver 30, i.e. in tube 40, the gaseous mixture contains 70% by volume oxygen. This is due to the fact that the culture arriving at 60 in the carbonator is very rich in dissolved oxygen resulting from the photosynthesis. At the outlet from the solar receiver, i.e. in the purge tubes 48, the gaseous mixture contains 75% by volume of oxygen. Thus, there is a 70 to 75% by volume oxygen enrichment in the solar receiver 30 as a result of the confinement of the culture medium.

The partial deoxygenation or oxygen desorption lowers the oxygen content of the gaseous phase by 70 to 75%. Under these oxidizing conditions, the cultured microalgae react by synthesizing antioxidants.

In particular, the microalga Porphyridium cruentum reacts by producing SOD at a mean rate of 10 to 20 U (NBT)/ml of culture, i.e. $5 \times 10^6$ to $20 \times 10^6$ $U/m^3$ and vitamin C at a rate of 5 to 7 g/kg. However, the microalga Haematococcus pluvialis reacts by producing vitamin E at a rate of 4 to 5 g/kg of microalgae and gamma-tocopherol at a rate of 0.5 to 1 g/kg of microalgae.

The apparatus shown in FIG. 2 also has a branch pipe 68 equipped with a valve 70 mounted on the outlet pipe 60. The pipe 68 issues into a vessel 70 used for collecting the microalgae and the culture medium after a culture cycle with a view to extracting the antioxidants therefrom.

The conditions favorable for the production of antioxidants are high photosynthetic activity conditions. It is also possible to optimize these conditions on a scale of a 10 to 20 days culture cycle or run. The photosynthetic activity of the microalgae is at a maximum at the start of the run, i.e. in the exponential growth phase and this is illustrated by the following example.

During a run carried out on a *Porphiridium cruentum* culture, the inventors noted the following SOD contents:

5th day:
  25 U (NBT)/ml of culture
  (1.0 g dm/l of culture), i.e.
  25,000 U/g of culture.
10th day:
  31 U (NBT)/ml of culture
  (1.3 g dm/l of culture) i.e.
  24,000 U/g of culture.
17th day:
  27 U (NBT)/ml of culture
  (1.8 g dm/l of culture) i.e.
  15,000 U/g of culture.
26th day:
  3 U (NBT)/ml of culture
  2.0 g dm/l of culture) i.e.
  1,500 U/g of culture.

This example makes it clear that the maximum antioxidant production takes place between the 1st and 10th days of a run.

Similar measurements were carried out during a run with *Heamatococcus pluvialis* as the microalga. The inventors noted that following tocopherol contents in the microalgae:

2nd day:
  4,500 ppm of alpha-tocopherol
  660 ppm of gamma-tocopherol
20th day:
  80 ppm of alpha-tocopherol
  130 ppm of gamma-tocopherol.

According to the invention, the microorganisms are cultured in the closed photobioreactor under natural lighting conditions, i.e. with an alternation of daylight and night. The assimilation of $CO_2$ by these microorganisms and consequently the production of $O_2$ are directly linked with the light intensity. Therefore they are at an optimum at midday.

Figure 3:
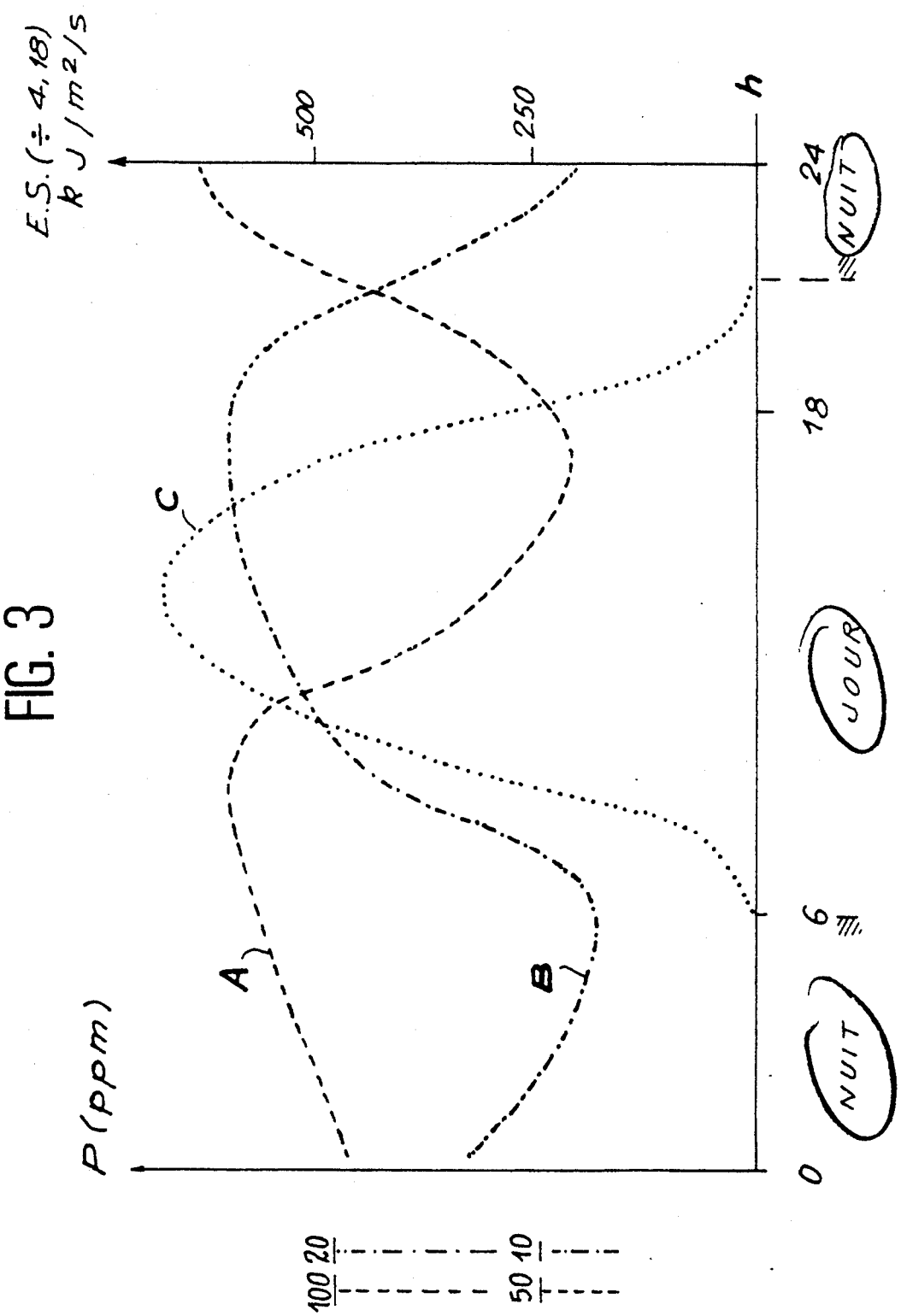
FIG. 3 the evolution of the photosynthetic activity in the culture medium during one day.

The graph of FIG. 3 reveals the evolution of the dissolved $CO_2$ pressure and the dissolved oxygen pressure in the culture medium during one day. The pressures of these gases are given in parts per million. Curve A gives the $CO_2$ pressures and curve B and $O_2$ pressures. Curve C gives the solar energy ES during the day and is expressed in kilojoules/$m^2$/s.

These curves make it clear that the best antioxidant production conditions occur between midday and 6 p.m., so that the antioxidants are collected during this period.

Figure 4:
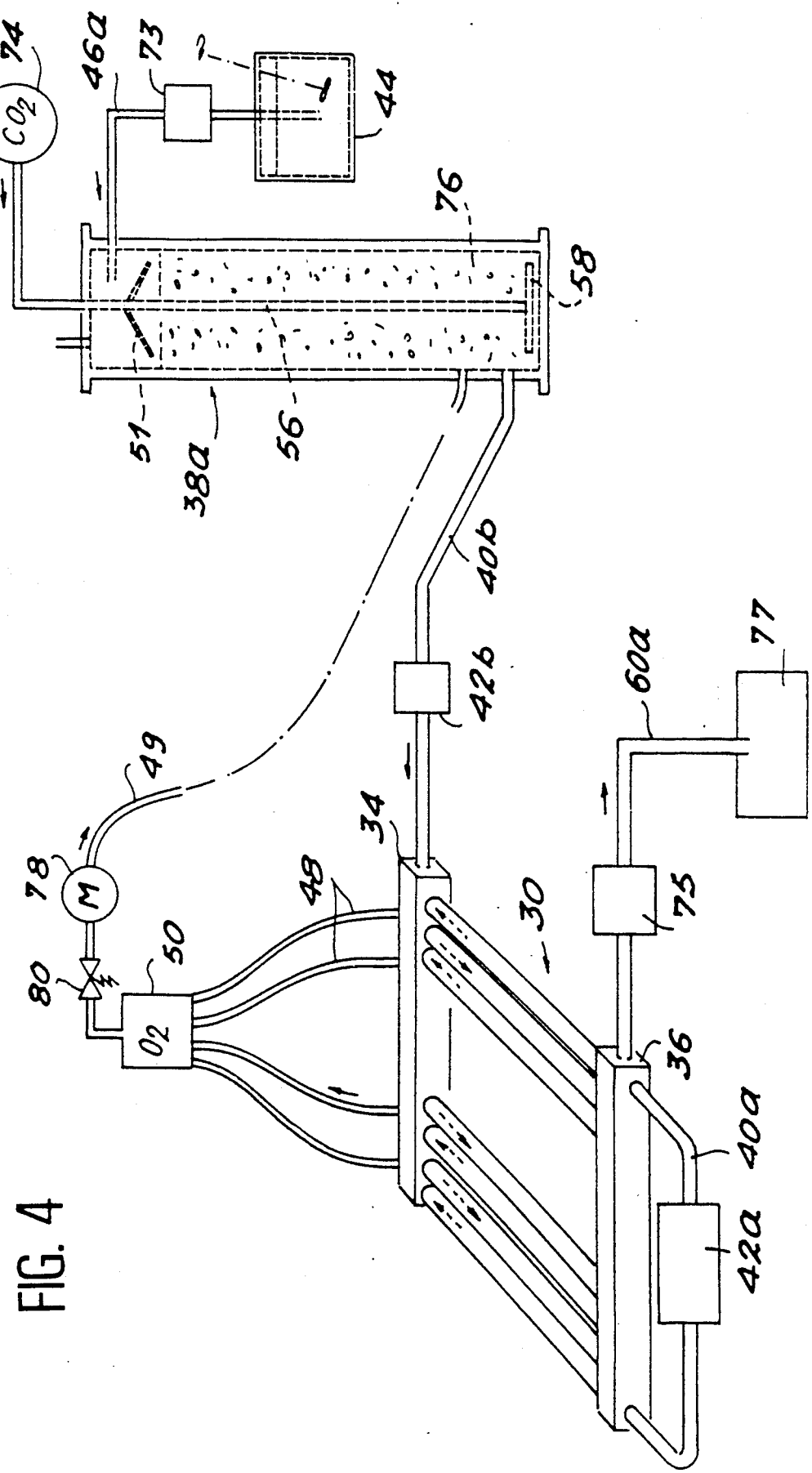
FIG. 4 diagrammatically a photobioreactor for the production of microalgae according to the invention and operating continuously.

The culture of the microalgae and therefore the production of antioxidants can also take place continuously with the aid of the photobioreactor shown in FIG. 4. The constituent elements of the said photobioreactor identical to those of the photobioreactor of FIG. 2 carry the same references.

As in FIG. 2, the photobioreactor has a tubular solar receiver 30 equipped with upstream and downstream collectors 34 and 36. A pump 42a mounted on a pipe 40a links the inlet and outlet of the collector 34 and functions in a continuous manner. It ensures the continuous circulation of the culture medium containing the microalgae in the solar receiver 30. The assembly constituted by the solar receiver, the pipe 40a and the pump 42a forms a closed or sealed assembly, i.e. the microorganisms do not pass out of it.

The nutrient medium prepared accompanied by stirring in the vessel 44 is introduced continuously in the present case at the top of the carbonator 38a by means of a supply pipe 46a equipped with a continuously operating pump 73, which also regulates the flow rate of the nutrient medium and therefore the nutrient medium replacement rate (once daily).

The immersion tube 56, equipped with its fritted glass 58 at its immersed end, makes it possible to supply $CO_2$ in countercurrent with the nutrient medium to the carbonator 38a.

In order to improve the dissolving of the $CO_2$ gas injected under pressure by means of the tank 74 fitted at the inlet of the immersion tube 56, the column of the carbonator is equipped with a lining 76 of the Raschig ring or Bert support type.

The carbonated nutrient medium is then injected into the solar receiver 30 by a supply pipe 40b linking the base of the carbonator 30a to the collector 34 of the solar receiver 30. The said pipe 40b is equipped with a continuously operating pump 42b regulated to the same flow rate or delivery as the pump 73 and 75.

At the outlet from the solar receiver 30, a pipe 60a equipped with pump 75 makes it possible to continuously supply of the culture medium containing the microorganism to a collecting vessel 77, with a view to the extraction of the antioxidants.

As previously, in the solar receiver 30, the photosynthesis brings about a dissolved oxygen enrichment of the culture. The oxygen-containing gas pockets formed are discharged from the receiver 30 by purge tubes 48 in the direction of the oxygen collector 50, which is equipped with a manometer 78 for measuring the pressure of the oxygen-enriched purge gas.

When the pressure is between 0.4 and $0.5.10^5$ Pa, an electrovalve 80 releases the accumulated gas into the collector 50. This gas is then reinjected by the pipe 49 at the bottom of the carbonator 38a, in such a way that the gaseous oxygen resulting from the photosynthesis dissolves in the culture medium. As previously, the accumulation of the gas in the solar receiver 30 causes a dissolved oxygen enrichment.

In order to increase the dissolved $O_2$ concentration in the liquid medium of the photobioreactor, it is desirable to make it operate under an overpressure. In the example shown, the solar receiver tubes 32 are unable to resist a pressure above $0.5.10^5$ Pa. In addition, the triggering of the electrovalve 80 takes place at between 0.4 and $0.5.10^5$ Pa. The normal pressure of the oxygen-enriched gas is between 0.1 and $0.2.10^5$ Pa.

In the photobioreactor shown in FIG. 2, the carbonator 38 does not have a lining, unlike in the case of the carbonator 38a of FIG. 4 due to the fact that in batch operation, the liquid medium containing the microorganisms passes through the carbonator and would adhere to the lining. Only the gases and nutrient medium circulate in the carbonator 38a.

In order to further improve the oxygen enrichment of the culture medium, it is possible to replace the pressurized $CO_2$ tank 74 of the photobioreactor of FIG. 4 by the recovery system 52-54-66 for the oxygen desorbed in the carbonator shown in FIG. 2.

With *Porphyridium cruentum* cultured and treated according to the invention, it is possible to obtain $5 \times 10^6$ to $20 \times 10^6$ NBT units of SOD in 1000 liters of culture, which corresponds to the production of 9 to 36 g of $SOD/m^3$ of culture. Under these conditions, solar receivers 30 distributed over a one hectare water surface and operating for 200 days every year will make it possible to produce 90 to 360 kg or SOD.

We claim:

1. Process for the production and extraction of antioxidants, comprising the following stages:

(a) culturing in a closed photobioreactor of photosynthetic microorganisms suspended in a liquid culture medium for producing oxygen and antioxidants, the oxygen produced by the microorganisms by photosynthesis being collected and reinjected into the culture medium, said microorganisms being chosen from the group consisting of rhodophyceae and chlorophyceae, said antioxidants being chosen from the group consisting of superoxide dismutase, vitamin C and tocopherols, (b) separating the microorganisms from the culture medium, (c) dispersing in a solution the microorganisms separated in (b), (d) crushing the dispersed microorganisms, (e) adding solvent to the solution obtained in (d) in order to solubilize the antioxidants produced by the microorganisms and then (f) separating the liquid and solid phases present.

2. Process according to claim 1, characterized in that stage (b) is performed during an exponential growth phase of the microorganisms.

3. Process according to claim 1, characterized in that the microorganisms are cultured under natural lighting conditions and in that stage (b) is performed in the afternoon.

4. Process according to claim 1, characterized in that it comprises a stage (1) of treating the culture medium (1) in order to increase the production of antioxidants.

5. Process according to claim 1, characterized in that the solvent is an organic solvent or vegetable or mineral oil.

6. Process according to claim 1, characterized in that stages (d), (a) and (f) are performed at approximately 4° C.

7. Process according to claim 1, characterized in that the liquid phases obtained in (f) are concentrated and then purified.

8. Process according to claim 1, characterized in that the culture medium separated in (b) is concentrated and then purified.

9. Process according to claim 1, characterized in that the solution of stage (c) contains 20 to 100 g/l of dry microorganisms.

10. Process according to claim 1, characterized in that the oxygen produced by photosynthesis is reinjected under pressure into the culture medium.

11. Process according to claim 1, characterized in that the microorganisms are chosen from among *Porphyridium cruentum* and *Haematococcus pluvialis*.

12. A process for the production and extraction of antioxidants, comprising the following steps:

(a) culturing in a closed photobioreactor of photosynthetic microorganisms suspended in a liquid culture medium for producing oxygen and antioxidants, collecting the oxygen produced by the microorganisms by photosynthesis and reinjecting the collected oxygen into the culture medium, heating said culture medium to increase production of antioxidants, said microorganisms being chosen form the group consisting of rhodophyceae and chlorophyceae, said antioxidants being chosen from the group consisting of superoxide dismutase, vitamin C and tocopherols, (b) separating the microorganisms from the culture medium, (c) dispersing in a solution the microorganisms separated in step (b), (d) crushing the dispersed microorganisms,
(e) adding solvent to the solution obtained in (d) in order to solubilize the antioxidants produced by the microorganisms and then
(f) separating the liquid and solid phases present.

13. A process as claimed in claim 12, wherein said microorganism is chosen from the group consisting of *Porphyridium cruentum* and *Haematococcus pluvialis* and said solvent is an organic solvent.

14. A process as claimed in claim 12, wherein said heating step to increase production of antioxidants is followed by subjecting the culture media to ionization to further increase production of antioxidants.

15. A process as claimed in claim 4, wherein said microorganism is chosen from the group consisting of *Porphyridium cruentum* and *Haematococcus pluvialis*, said solvent is an organic solvent, said treating step is heating the culture medium, and said antioxidants are superoxide-dismutase enzymes.

16. A process for the production and extraction or antioxidants, comprising the following steps:
(a) culturing in a closed photobioreactor of photosynthetic microorganisms suspended in a liquid culture medium for producing oxygen and antioxidants, collecting the oxygen produced by the microorganisms by photosynthesis and reinjecting the collected oxygen into the culture medium, subjecting said culture medium ionization to increase production of antioxidants, said microorganisms being chosen from the group consisting of rhodophyceae and chlorophyceae, said antioxidants being chosen from the group consisting of superoxide dismutase, vitamin C and tocopherols,
(b) separating the microorganisms from the culture medium,
(c) dispersing in a solution the microorganisms separated in step (b),
(d) crushing the dispersed microorganisms,
(e) adding solvent to the solution obtained in (d) in order to solubilize the antioxidants produced by the microorganisms, and then
(f) separating the liquid and solid phases present.

17. A process as claimed in claim 16, wherein said microorganism is chosen from the group consisting of *Porphyridium cruentum* and *Haematococcus pluvialis* and said solvent is an organic solvent.

* * * * *